(12) United States Patent
Monteiro

(10) Patent No.: US 9,874,548 B2
(45) Date of Patent: *Jan. 23, 2018

(54) CHEMIRESISTIVE SENSORS, DOWNHOLE TOOLS INCLUDING SUCH SENSORS, AND RELATED METHODS

(71) Applicant: Baker Hughes Incorporated, Houston, TX (US)

(72) Inventor: Othon R. Monteiro, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/400,349

(22) Filed: Jan. 6, 2017

(65) Prior Publication Data

US 2017/0115263 A1   Apr. 27, 2017

Related U.S. Application Data

(63) Continuation of application No. 14/874,578, filed on Oct. 5, 2015, now Pat. No. 9,562,430.

(51) Int. Cl.
*E21B 49/08* (2006.01)
*E21B 49/00* (2006.01)
(Continued)

(52) U.S. Cl.
CPC ......... *G01N 33/0044* (2013.01); *E21B 49/08* (2013.01); *G01N 27/4141* (2013.01);
(Continued)

(58) Field of Classification Search
CPC ...... G01N 1/22; G01N 1/2202; G01N 1/2294; G01N 1/4022; G01N 27/04; G01N 27/12;
(Continued)

(56) References Cited

U.S. PATENT DOCUMENTS 4,659,343 A   4/1987 Kelly
4,822,465 A   4/1989 Jones et al.
(Continued)

FOREIGN PATENT DOCUMENTS

WO   2013190093 A2   12/2013

OTHER PUBLICATIONS

International Search Report for International Application No. PCT/US2016/055168 dated Jan. 9, 2017, 3 pages.
(Continued)

*Primary Examiner* — Maureen Wallenhorst
(74) *Attorney, Agent, or Firm* — TraskBritt

(57) ABSTRACT

A method of detecting an analyte includes vaporizing at least a portion of a fluid within a wellbore, passing the vaporized fluid adjacent a chemiresistive sensing element coupled to a drill string within the wellbore and sensing a resistivity of the chemiresistive sensing element. A sensor for detecting an analyte includes an expansion device for vaporizing a portion of a fluid within a wellbore, a chemiresistive sensing element configured to contact the vaporized fluid within the wellbore and a controller configured to pass a current through the chemiresistive sensing element and calculate a resistance of the chemiresistive sensing element in contact with the gaseous portion of the fluid. An earth-boring tool may include a bit body coupled to a drill string and the sensor.

19 Claims, 4 Drawing Sheets

(51) Int. Cl.

| | |
|---|---|
| *G01N 27/414* | (2006.01) |
| *G01N 27/12* | (2006.01) |
| *G01N 27/04* | (2006.01) |
| *G01N 33/28* | (2006.01) |
| *G01N 33/24* | (2006.01) |
| *G01N 33/00* | (2006.01) |
| *G01N 1/22* | (2006.01) |
| *E21B 10/00* | (2006.01) |
| *E21B 21/00* | (2006.01) |
| *E02D 1/00* | (2006.01) |

(52) U.S. Cl.
CPC ..... *G01N 33/0016* (2013.01); *G01N 33/2823* (2013.01); *E02D 1/00* (2013.01); *E21B 10/00* (2013.01); *E21B 21/00* (2013.01); *E21B 49/003* (2013.01); *E21B 49/087* (2013.01); *E21B 49/088* (2013.01); *E21B 2049/085* (2013.01); *G01N 1/2294* (2013.01); *G01N 27/04* (2013.01); *G01N 27/12* (2013.01); *G01N 33/24* (2013.01); *Y10T 436/184* (2015.01)

(58) Field of Classification Search
CPC ............... G01N 27/125; G01N 27/126; G01N 33/0044; G01N 33/24; G01N 33/241; G01N 33/2823; G01N 33/20; G01N 27/4141; G01N 33/0016; Y10T 436/182; Y10T 436/184; Y10T 436/255; Y10T 436/25875; E21B 49/00; E21B 49/087; E21B 49/088; E21B 49/003; E21B 10/00; E21B 21/00; E21B 49/08; E21B 2049/085; E02D 1/00
USPC ......... 436/25, 28, 30, 73, 80, 119, 120, 121, 436/149, 151, 178, 181; 422/82.01, 422/82.02, 83, 98, 535
See application file for complete search history.

(56) References Cited

U.S. PATENT DOCUMENTS

| | | | |
|---|---|---|---|
| 5,147,561 | A | 9/1992 | Burge et al. |
| 5,302,935 | A | 4/1994 | Chatterjee |
| 5,759,493 | A | 6/1998 | Raisanen |
| 5,859,430 | A | 1/1999 | Mullins et al. |
| 7,003,405 | B1 | 2/2006 | Ho |
| 7,516,654 | B2 | 4/2009 | DiFoggio |
| 8,519,713 | B2 | 8/2013 | Lawrence et al. |
| 9,562,430 | B1 * | 2/2017 | Monteiro .............. E21B 49/003 |
| 2003/0079876 | A1 | 5/2003 | Underdown |
| 2003/0134426 | A1 | 7/2003 | Jiang et al. |
| 2004/0159149 | A1 | 8/2004 | Williams et al. |
| 2005/0205256 | A1 | 9/2005 | DiFoggio |
| 2006/0243603 | A1 | 11/2006 | Jiang et al. |
| 2009/0090176 | A1 | 4/2009 | Toribio et al. |
| 2011/0151574 | A1 * | 6/2011 | Chen ..................... B82Y 30/00 |
| | | | 436/149 |
| 2013/0134981 | A1 | 5/2013 | Liu et al. |
| 2014/0138259 | A1 | 5/2014 | Mickelson et al. |

OTHER PUBLICATIONS

International Written Opinion for International Application No. PCT/US2016/055168 dated Jan. 9, 2017, 10 pages.

Gutes et al., Graphene Decoration with Metal Nanoparticles: Towards Easy Integration for Sensing Applications, Nanoscale, (2012), vol. 4, pp. 438-440.

Mickelson et al., Low-Power, Fast, Selective Nanoparticle-Based Hydrogen Sulfide Gas Sensor, Applied Physics Letters, (2012), vol. 100, pp. 173110-1-173110-4.

Mills et al., Hydrogen Sulfide Drilling Contingency Plan, IDP Technical Note 33, (2006), pp. 1-33.

Pandey et al., A Review of Sensor-Based Methods for Monitoring Hydrogen Sulfide. Trac Trends in Analytica Chemistry, Feb. 2012, vol. 32, pp. 87-99.

* cited by examiner

CHEMIRESISTIVE SENSORS, DOWNHOLE TOOLS INCLUDING SUCH SENSORS, AND RELATED METHODS

CROSS-REFERENCE TO RELATED APPLICATION

This application is a continuation of U.S. patent application Ser. No. 14/874,578, filed Oct. 5, 2015, now U.S. Pat. No. 9,562,430, issued Feb. 7, 2017, the disclosure of which is hereby incorporated herein in its entirety by this reference.

FIELD

Embodiments of the present disclosure relate generally to chemiresistive sensors, and methods of using such sensors in conjunction with forming, enlarging, or maintaining a wellbore, as well as in production of hydrocarbons from subterranean formations.

BACKGROUND

Drilling fluids are used in the drilling of subterranean oil and gas wells. In rotary drilling, drilling fluids, also known as drilling muds, or simply "muds," are used for cooling and lubricating drill bits, lubricating drill pipes, carrying cuttings and other materials from the hole to the surface, and exerting a hydrostatic pressure against the borehole wall to prevent the flow of fluids from the surrounding formation into the borehole. Drilling fluids can become contaminated by compounds encountered in drilling.

For example, gases commonly encountered in subterranean formations include methane ($CH_4$), carbon dioxide ($CO_2$), carbon monoxide (CO), nitrogen ($N_2$), ammonia ($NH_3$), and hydrogen sulfide ($H_2S$). Some of the gases have negative effects and impose additional costs on drilling operations. For example, $H_2S$ is toxic, flammable, and corrosive. $H_2S$ collects at ground level, which presents a risk that $H_2S$ will accumulate over time. In certain concentrations and over time, $CO_2$ may be corrosive to processing equipment by reacting with steel. Because of the properties of gases encountered in drilling operations, it would be beneficial to have a reliable method of determining the concentration of such gases in a subterranean formation and in drilling fluids used forming and servicing subterranean formations.

$H_2S$, $CO_2$, CO, $NH_3$, and other analytes of interest in production fluids in oil and gas exploration and production can be present in an oil phase, an aqueous phase (e.g., a brine) or even in a gaseous phase. Thus, effective measurement of any such analyte should account for different phases in which the analyte may be present.

BRIEF SUMMARY

In some embodiments, a method of detecting an analyte includes vaporizing at least a portion of a fluid within a wellbore, passing the vaporized fluid adjacent a chemiresistive sensing element coupled to a drill string within the wellbore and sensing a resistivity of the chemiresistive sensing element.

In other embodiments, a sensor for detecting an analyte includes an expansion device for vaporizing a portion of a fluid within a wellbore, a chemiresistive sensing element configured to contact the vaporized fluid within the wellbore and a controller configured to pass a current through the chemiresistive sensing element and measure the resistance of the chemiresistive sensing element in contact with the gaseous portion of the fluid. An earth-boring tool may include a bit body coupled to a drill string and the sensor.

BRIEF DESCRIPTION OF THE DRAWINGS

While the specification concludes with claims particularly pointing out and distinctly claiming what are regarded as embodiments of the present disclosure, various features and advantages of embodiments of the disclosure may be more readily ascertained from the following description of example embodiments of the disclosure when read in conjunction with the accompanying drawings, in which:

DETAILED DESCRIPTION

Figure 1:
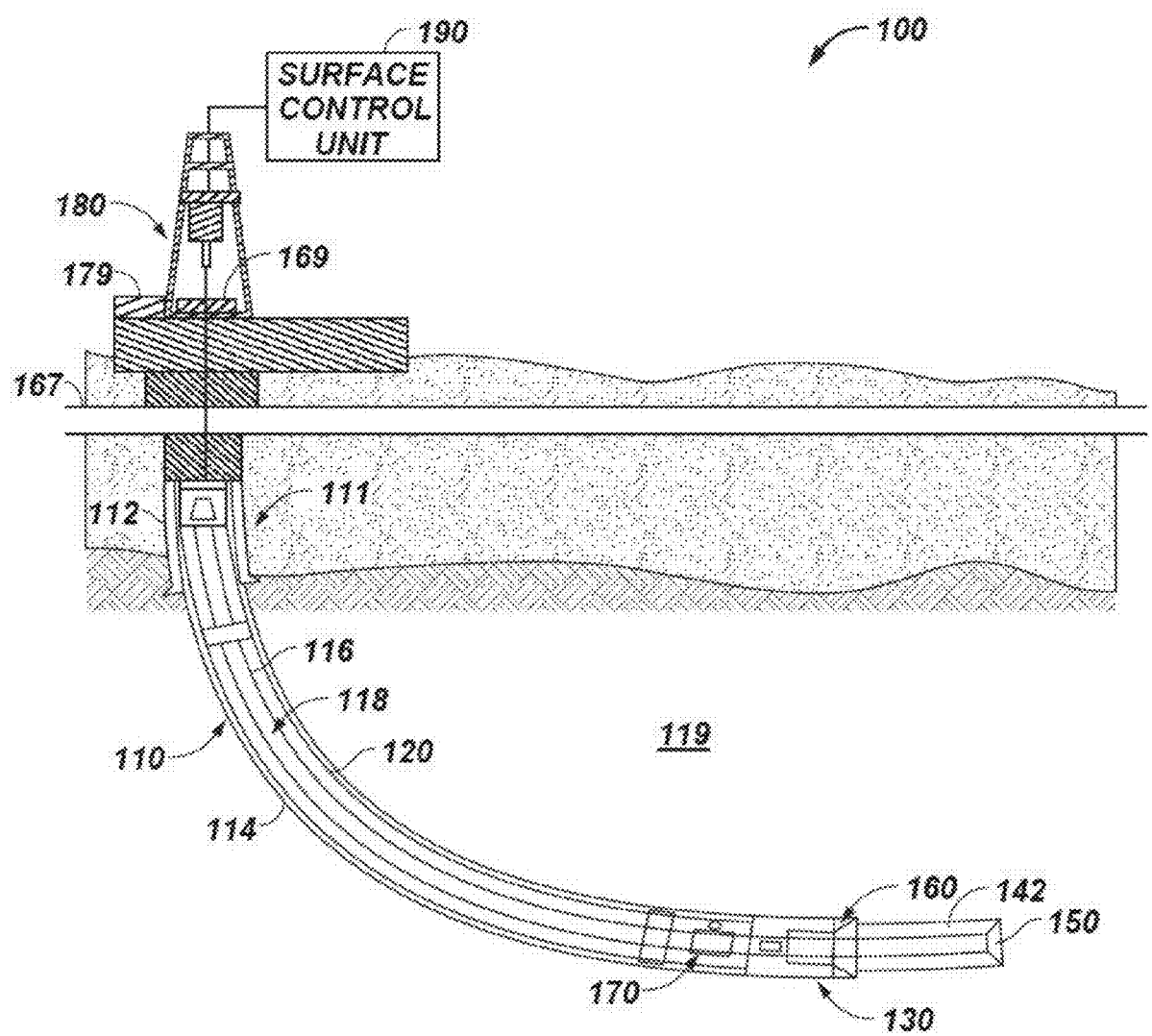
FIG. 1 is a schematic diagram of a wellbore system comprising a drill string that includes a sensor according to one embodiment of the disclosure herein.

The illustrations presented herein are not meant to be actual views of any particular material, apparatus, system, or method, but are merely idealized representations employed to describe certain embodiments. For clarity in description, various features and elements common among the embodiments may be referenced with the same reference numerals.

Methods and sensors as disclosed herein may be used for detecting an analyte in a fluid in situ. For example, a fluid used or encountered in a subterranean formation may be tested without transporting the fluid to the surface. The methods may generally include passing a gaseous portion of the fluid adjacent a chemiresistive sensing element and sensing a resistivity of the chemiresistive sensing element.

The fluid to be analyzed may include, for example, a production fluid, a drilling fluid, a workover fluid, etc. A sample of the fluid may be subjected to a reduced pressure and/or heat to vaporize at least a portion of the fluid. A portion of the fluid may remain in a liquid phase, and the vapor phase may be separated from the liquid phase. The vapor phase may then be transferred to a sensor where one or more components of the vapor phase may be analyzed. For example, the vapor phase may be tested to determine a concentration of hydrogen sulfide ($H_2S$), carbon dioxide ($CO_2$), carbon monoxide, (CO), ammonia ($NH_3$), a low-molecular-weight hydrocarbon, etc. In some embodiments, all or substantially all of a specific analyte in a given volume of fluid is vaporized prior to entering the sensing region, so that the concentration of analyte in the sample can be accurately determined.

FIG. 1 is a schematic diagram of an example of a drilling system 100 utilizing the apparatus and methods disclosed herein. FIG. 1 shows a wellbore 110 that includes an upper section 111 with a casing 112 installed therein and a lower section 114 that is being drilled with a drill string 118. The drill string 118 includes a tubular member 116 that carries a drilling assembly 130 at its bottom end. The tubular member 116 may be formed by joining drill pipe sections or may be coiled tubing. A drill bit 150 (also referred to as the "pilot bit") is attached to the bottom end of the drilling assembly 130 for drilling a first, smaller diameter borehole 142 in the formation 119. A reamer 160 may be placed above or uphole of the drill bit 150 in the drill string 118 to enlarge the borehole 142 to a second, larger diameter borehole 120. The terms wellbore and borehole are used herein as synonyms.

The drill string 118 extends to a rig 180 at the surface 167. The rig 180 shown is a land rig for ease of explanation. The apparatus and methods disclosed herein equally apply when an offshore rig is used for drilling underwater. A rotary table 169 or a top drive may rotate the drill string 118 and the drilling assembly 130, and thus the pilot bit 150 and reamer bit 160, to respectively drill boreholes 142 and 120. The rig 180 also includes conventional devices, such as mechanisms to add additional sections to the tubular member 116 as the wellbore 110 is drilled. A surface control unit 190, which may be a computer-based unit, is placed at the surface for receiving and processing downhole data transmitted by the drilling assembly 130 and for controlling the operations of the various devices and sensors 170 in the drilling assembly 130. A drilling fluid from a source 179 thereof is pumped under pressure through the tubular member 116 that discharges at the bottom of the pilot bit 150 and returns to the surface via the annular space (also referred to as the "annulus") between the drill string 118 and an inside wall of the wellbore 110.

During operation, when the drill string 118 is rotated, both the pilot bit 150 and reamer bit 160 rotate. The pilot bit 150 drills the first, smaller diameter borehole 142, while simultaneously the reamer bit 160 drills the second, larger diameter borehole 120. The earth's subsurface may contain rock strata made up of different rock structures that can vary from soft formations to very hard formations.

Figure 2:
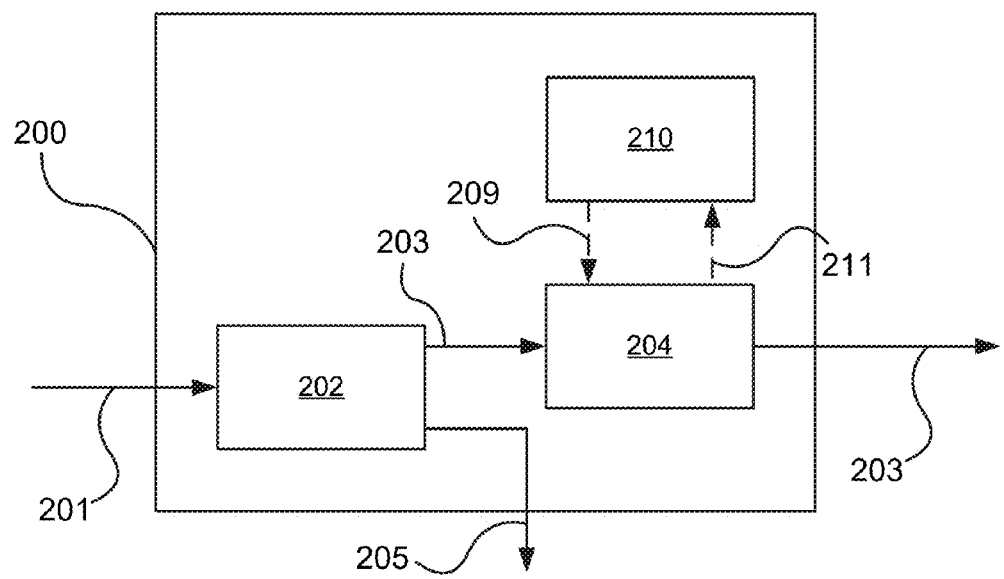
FIG. 2 is a simplified block flow diagram illustrating an embodiment of a sensor.

The sensors 170 in the drilling assembly 130 may include a sensor 200, as depicted in a simplified schematic diagram in FIG. 2. The sensor 200 may be within or attached to a surface of the drilling assembly 130. The sensor 200 includes an expansion device 202 and a gas analyzer 204. The expansion device 202 is configured to receive a fluid 201 within a borehole 142, 120 (FIG. 1), and to form a vapor fraction 203 and, optionally, a liquid fraction 205 from the fluid 201. The vapor fraction 203 is tested in the gas analyzer 204. The gas analyzer 204 may receive an electrical signal 209 from a controller 210, and may provide an electrical signal 211 to the controller 210. The controller 210 may include, for example, processor, a memory, a solid-state device, a power source, etc. The controller 210 may communicate with an external source (e.g., the surface control unit 190 shown in FIG. 1) to transmit and receive information (e.g., receive instructions and transmit data collected).

Figures 3A, 3B:
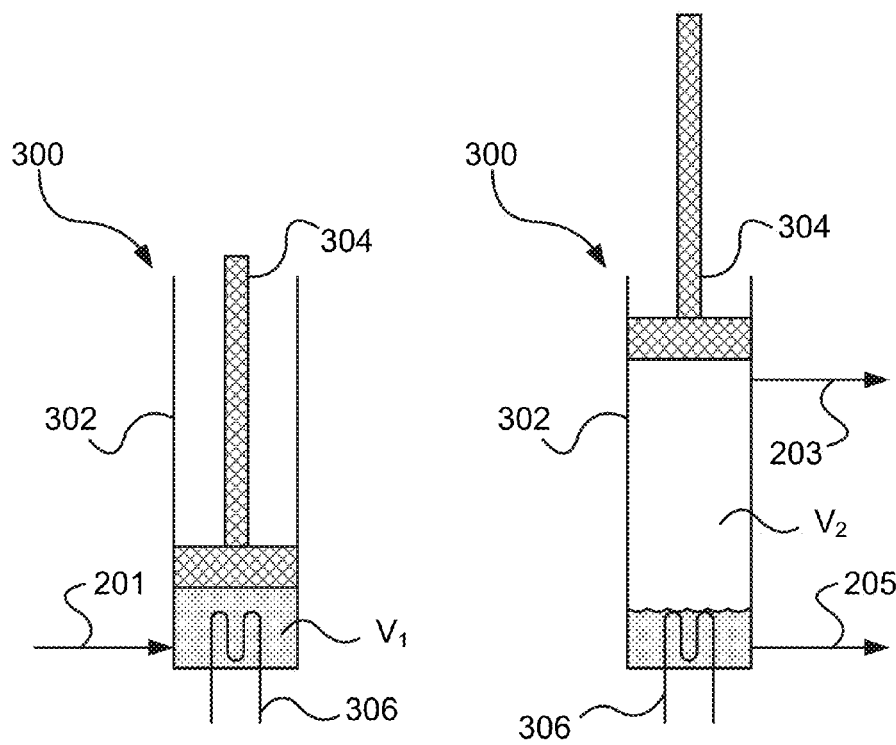
FIGS. 3A and 3B are simplified cross-sectional views of a piston assembly that may be used in the sensor of FIG. 2.

The expansion device 202 may include any device for decreasing a total pressure on the fluid 201. For example, and as discussed in further detail below, the expansion device 202 may include one or more of a piston, a venturi tube, an expansion tank, a heater, an ultrasonic vaporizer, or any other device to vaporize and expand a fluid. The total pressure is typically decreased by increasing the volume that the fluid 201 occupies. FIGS. 3A and 3B are simplified diagrams depicting a piston assembly 300 that may be used in the expansion device 202. As shown in FIG. 3A, the fluid 201 may enter the piston assembly 300 into a volume bounded by a piston wall 302 and a piston head 304. The piston head 304 may be at or near a position that minimizes the interior volume of the piston assembly 300 (i.e., down, in the orientation shown in FIG. 3A). Thus, when the piston head 304 moves upward, as shown in FIG. 3B, the interior volume within the piston assembly 300 increases. The vapor fraction 203 may form (and, optionally, may separate from the liquid fraction 205, if any of fluid 201 remains in liquid form) due to the decrease in pressure that accompanies the increase in volume within the piston assembly 300. For example, the decrease in pressure of the fluid 201 may release dissolved gases from the fluid 201. The vapor fraction 203 can then be transferred from the piston assembly 300 to the gas analyzer 204 (see FIG. 2) for analysis. The liquid fraction 205, if present, may be discarded (e.g., returned to the borehole 142, 120 (FIG. 1).

The ratio of the interior volume $V_2$ of the piston assembly 300 when in the expanded position (FIG. 3B) to the interior volume $V_1$ of the piston assembly 300 when the fluid 201 enters is the expansion ratio $$\left(\text{i.e., } = \frac{V_2}{V_1}\right)$$

or decompression ratio. The expansion ratio of the piston assembly 300 may be, for example, from about 10 to about 1000. The amount and composition of the vapor fraction 203 produced may vary based on the expansion ratio. Thus, the expansion ratio of the piston assembly 300 may be selected based on the fluid 201 to be tested and the expected composition thereof. For example, for a fluid 201 to be tested for highly volatile gases (e.g., low boiling point, as compared to other components of the fluid 201), a relatively lower expansion ratio may be selected. For a fluid 201 to be tested for gases having a lower volatility, a relatively higher expansion ratio may be selected. Furthermore, the expansion ratio may vary based on the sensitivity of the gas analyzer 204 to detect the analyte of interest. For a relatively sensitive gas analyzer 204, a smaller expansion ratio may be selected, due to the ability of the gas analyzer 204 to measure low concentrations. The expansion ratio may vary based on the whether all or part of the fluid is to be vaporized (i.e., whether a liquid fraction 205 will remain after expansion). In some embodiments, the expansion ratio of the piston assembly 300 may be selected to be from about 25 to about 250, such as from about 50 to about 100, or at least about 60.

In some embodiments, the expansion device 202 (FIG. 2) may include a heating element 306 instead of or in addition to the piston assembly 300. For example, the heating element 306 may be integrated with the piston assembly 300, as shown in FIGS. 3A and 3B. In other embodiments, the heating element 306 may be separate from the piston assembly 300. Thus, the heating element 306 may heat the fluid 201 before, during, or after the expansion of the fluid 201 in the piston assembly 300.

Heat from the heating element 306 may promote vaporization of at least a portion of the fluid 201 to form the vapor fraction 203. In some embodiments, the vapor fraction 203 may be all or substantially all of the fluid leaving the piston assembly 300. The heating element 306 may be an electrical resistance heater, a heat pump, a heated coil, or any other heating device. In some embodiments, the expansion device 202 may include an ultrasonic vaporizer (e.g., a transducer) to promote vaporization of the fluid 201.

Figure 4:
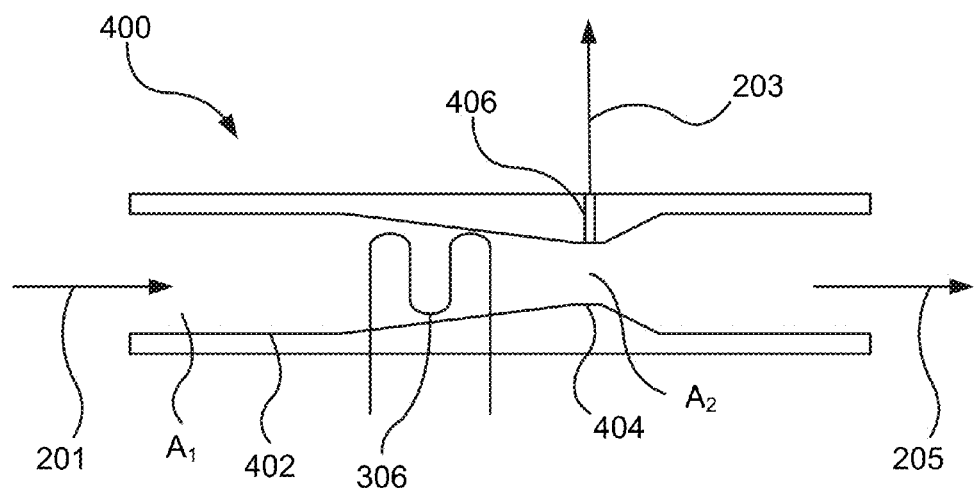
FIG. 4 is a simplified cross-sectional view of a venturi tube that may be used in the sensor of FIG. 2.

FIG. 4 is a simplified diagram depicting a venturi tube 400 that may be used in the expansion device 202. The fluid 201 may continuously flow through the venturi tube 400. The fluid 201 may flow with a first velocity at a first pressure in a straight section 402 of the venturi tube 400. At a throat 404, the fluid 201 flows at a second, higher velocity and at a second, lower pressure. At the throat 404, the fluid 201 may be in vapor phase. The vapor fraction 203 can be extracted through a port 406 and transferred to the gas analyzer 204 (see FIG. 2) for analysis. The remainder of the fluid 201 may return to a liquid phase after passing through the throat 404, and may leave the venturi tube 400 as the liquid fraction 205. The liquid fraction 205 may be discarded (e.g., returned to the borehole 142, 120 (FIG. 1).

The expansion ratio or decompression ratio of the venturi tube 400 may be defined as the ratio of the cross-sectional area $A_1$ of the straight section 402 to the cross-sectional area $A_2$ of the throat 404

$$\left(i.e., = \frac{A_1}{A_2}\right).$$

The expansion ratio of the venturi tube 400 may be, for example, from about 10 to about 1000. The expansion ratio may be selected as described above with respect to the piston assembly 300 (FIGS. 3A and 3B). In some embodiments, the expansion ratio of the venturi tube 400 may be selected to be from about 25 to about 250, such as from about 50 to about 100, or at least about 60.

In some embodiments, the venturi tube 400 may optionally include a heating element 306 to heat the fluid 201, as described above and shown in FIGS. 3A and 3B. Heat from the heating element 306, in conjunction with the Venturi effect, may promote vaporization of a portion of the fluid 201 to form the vapor fraction 203. The heating element 306 may be an electrical resistance heater, a heat pump, a heated coil, or any other heating device. In some embodiments, the venturi tube 400 may be coupled with another device to promote vaporization of the fluid, such as an ultrasonic vaporizer.

Figure 5:
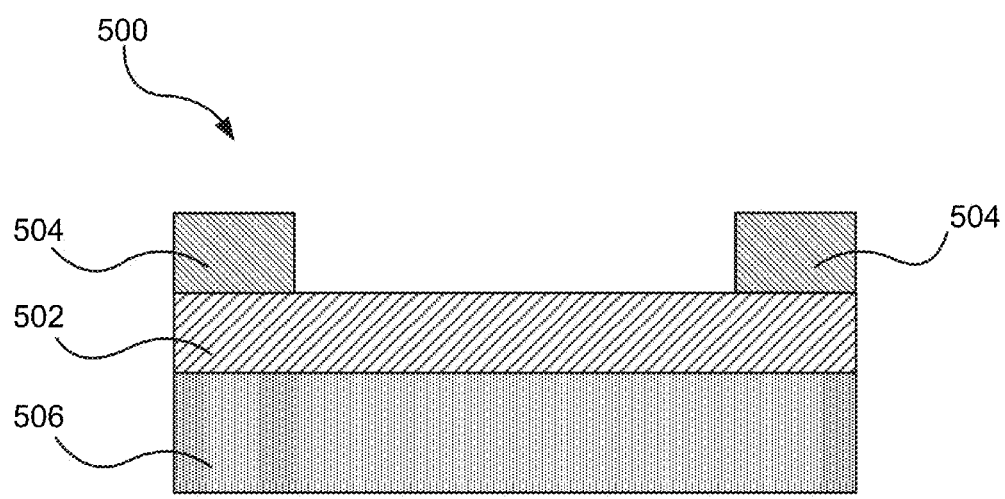
FIG. 5 is a simplified cross-sectional view of a chemiresistive sensor that may be used in the sensor of FIG. 2.

The gas analyzer 204 is configured to detect an analyte of interest in the vapor fraction 203 of the fluid 201. The gas analyzer 204 may include a sensor configured to measure changes in resistivity of sensing elements that result from exposing the sensing elements to the analyte of interest. Such a sensor may be referred to as a "chemiresistive sensor." FIG. 5 shows a simplified cross-section of a chemiresistive sensor 500, which may be a part of the gas analyzer 204 shown in FIG. 2. The chemiresistive sensor 500 includes a chemiresistive sensing element 502, which is configured to change its resistance based on the concentration of an analyte of interest adjacent to the chemiresistive sensing element 502. The chemiresistive sensing element 502 may be, for example, a material formed over a substrate. For example, the chemiresistive sensing element 502 may include a metal such as gold, silver, copper, indium, aluminum, etc., or an alloy thereof. In some embodiments, the chemiresistive sensing element 502 may include a metal oxide, such as zinc oxide, a tungsten oxide, chromium titanium oxide, gallium oxide, molybdenum oxide, tin oxide, etc. In some embodiments, the chemiresistive sensing element 502 may include a conductive polymer or a polymer-matrix composite material, such as silicon rubber-graphite composite materials or carbon nanotube-filled polystyrene composite materials. The chemiresistive sensing element 502 may be a thin film having a thickness of, for example, less than about 100 µm, less than about 10 µm, less than about 1 µm, or even less than about 100 nm. In some embodiments, the chemiresistive sensing element 502 may be a film having a thickness of about 50 nm. The chemiresistive sensing element 502 may be a wire having a diameter of, for example, less than about 100 µm, less than about 10 µm, less than about 1 µm, or even less than about 100 nm. In some embodiments, the chemiresistive sensing element 502 may be a wire having a diameter of about 50 nm. Chemiresistive sensing elements are described in U.S. Pat. No. 5,302,935, "Renewable Gas Sensor, Renewable Gas Sensor Base and Method for Renewing a Gas Sensor," issued Apr. 12, 1994, the entire disclosure of which is hereby incorporated herein by this reference.

Electrodes 504 electrically connect to the chemiresistive sensing element 502, and may be electrically connected to a detector configured to measure resistance, such as in the surface control unit 190 (FIG. 1) or in the drilling assembly 130. The electrodes 504 may include one or more conductive elements, such as copper, silver, gold, etc. In some embodiments, the electrodes 504 may be electrically connected to an ohmmeter, and the electrical signal 209 (FIG. 2) may be an applied voltage and the electrical signal 211 (FIG. 2) may be a measurement of current passing through the chemiresistive sensing element 502 and the electrodes 504. The chemiresistive sensing element 502 may be bonded to or mounted on a substrate 506 for structural support and/or for electrically insulating the chemiresistive sensing element 502 from other parts of the drilling assembly 130.

Figure 6:
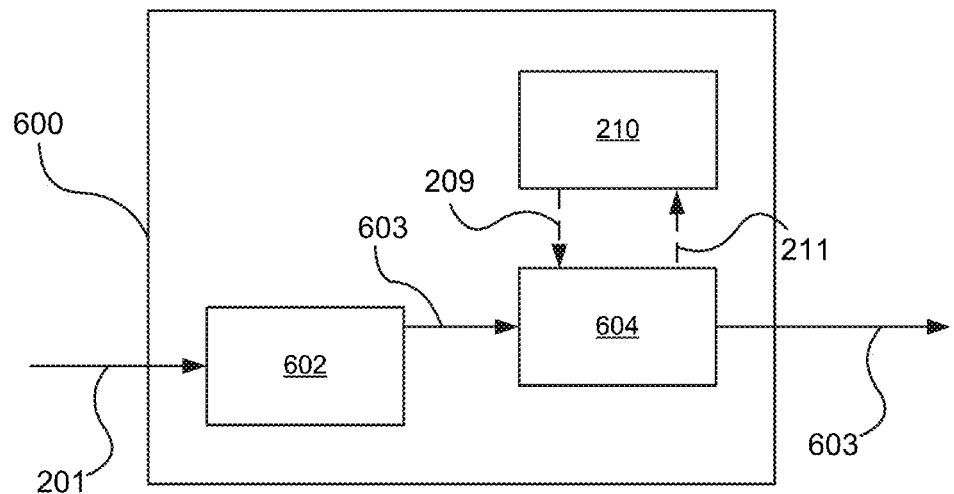
FIG. 6 is a simplified block flow diagram illustrating another embodiment of a sensor.

FIG. 6 is a simplified schematic diagram illustrating another sensor 600 that may be included as one of the sensors 170 in the drilling assembly 130 (FIG. 1). The sensor 600 may be within or attached to a surface of the drilling assembly 130. The sensor 600 includes an expansion device 602 and a gas analyzer 604. The expansion device 602 is configured to receive a fluid 201 within a borehole 142, 120 (FIG. 1), and vaporize at least a portion thereof, forming a test fluid 603. The test fluid 603 is tested in the gas analyzer 604. The sensor 600 differs from the sensor 200 shown in FIG. 2 in that the entire test fluid 603 may be transferred to the gas analyzer 604, even if not all of the test fluid 603 is in a vapor phase.

Conventional chemiresistive sensors typically have a short useful life when exposed directly to liquids, because the liquids tend to cause fouling or contamination of the sensing element. Furthermore, liquids tend to have a relatively larger influence on the electrical resistance of the sensing element than do gases, and thus a smaller detection range than gases. Thus, it may be beneficial to prevent liquids from directly contacting a chemiresistive sensor used in the gas analyzer 604.

Figure 7:
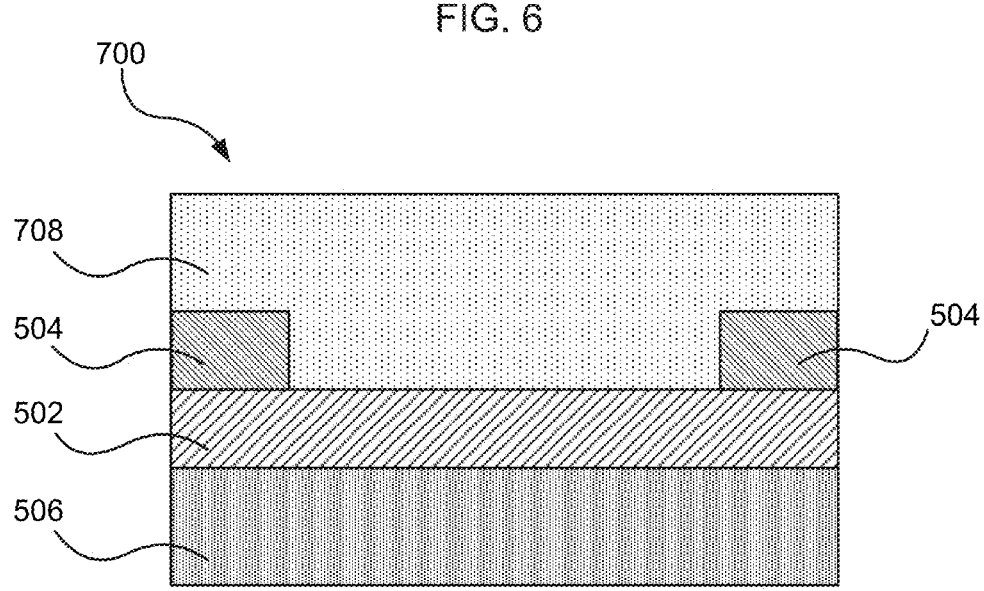
FIG. 7 is a simplified cross-sectional view of a chemiresistive sensor that may be used in the sensor of FIG. 6.

FIG. 7 shows a chemiresistive sensor 700 that includes a semipermeable membrane 708 configured to selectively allow diffusion of gaseous species at a higher rate than liquid species. The semipermeable membrane 708 as shown in FIG. 7 and described in further detail below may be incorporated into any of the embodiments described herein. The semipermeable membrane 708 may include, for example, a silicone rubber material or another polymeric separation membrane. In some embodiments, the semipermeable membrane 708 may include a structural material such as stainless steel having holes to allow gases to pass.

A diffusion rate of gaseous species through the semipermeable membrane 708 may be at least $10^3$ times a diffusion rate of liquid species, at least $10^4$ times a diffusion rate of liquid species, at least $10^5$ times a diffusion rate of liquid species, or even at least $10^6$ times a diffusion rate of liquid species. The semipermeable membrane 708 may be disposed over a chemiresistive sensing element 502 and electrodes 504, described previously with respect to FIG. 5. The semipermeable membrane 708 may partially or completely block the flow of liquids, and may protect the chemiresistive sensing element 502 from fouling and contamination. For example, if the analyte of interest is $H_2S$, the semipermeable membrane 708 may allow $H_2S$ to pass, but not hydrocarbons. In some embodiments, the semipermeable membrane 708 may selectively allow diffusion of different gases, and may block others. For example, the semipermeable membrane 708 may allow small molecules (e.g., $H_2S$, $CO_2$, $CH_4$, etc.) to diffuse therethrough, but may block larger molecules (e.g., $C_4H_{10}$, $C_5H_{12}$, etc.) (e.g., the diffusion rate of the larger molecules may be several orders of magnitude smaller than the diffusion rate of the smaller molecules).

The material(s) of the semipermeable membrane 708 may be selected based on the expected chemical composition of the fluid 201. In some embodiments, the semipermeable membrane 708 may include a material having pores selected to allow certain components of the fluid 201 to pass. For example, the semipermeable membrane 708 may include a porous polymer, porous glass, engineered alumina with drill pores, etc. In certain embodiments, transfer of the analyte of interest may be based on solubility of the analyte in the material of the semipermeable membrane 708, rather than on a physical path through the semipermeable membrane 708. For example, the analyte may dissolve in the material of the semipermeable membrane 708 at a rate high enough to allow transfer of the analyte through the semipermeable membrane 708 to the chemiresistive sensing element 502. In some embodiments, the semipermeable membrane 708 may include polyimides, polyacrylonitriles, polyethersulphones, alpha alumina, etc. The semipermeable membrane 708 may be a thin film having a thickness of up to about 1000 μm, and having pores with an average diameter of below about 50 nm. The semipermeable membrane 708 may include multiple layers of material, which may be of the same or different composition. For example, the semipermeable membrane 708 may include a layer of a polyacrylonitrile to separate liquids from gases, and may further include a layer of a polyimide to separate $H_2S$ or a cellulose ester membrane to separate $CO_2$. Thus, the material diffusing to the chemiresistive sensing element 502 may be enriched in $H_2S$ (or another analyte of interest). Semipermeable membranes are described in U.S. Patent App. Pub. 2003/0079876, "Method and System for Regeneration of a Membrane Used to Separate Fluids in a Wellbore," published May 1, 2003; and U.S. Pat. No. 4,659,343, "Process for Separating $CO_2$ from Other Gases," granted Apr. 21, 1987; and U.S. Pat. No. 7,516,654, "Method and Apparatus for Downhole Detection of $CO_2$ and $H_2S$ Using Resonators Coated with $CO_2$ and $H_2S$ Sorbents," issued Apr. 14, 2009, the entire disclosures of each of which are hereby incorporated herein by this reference.

Use of a chemiresistive sensor 700 having a semipermeable membrane 708 may limit the need to separate the fluid 201 into the vapor fraction 203 and the liquid fraction 205 (FIG. 2), and thus may simplify operational efficiency and reliability as compared to the sensor 200 (FIG. 2) equipped with the chemiresistive sensor 500 (FIG. 5) without a semipermeable membrane.

In some embodiments, the sensors 200, 600 shown and described may be capable of detecting analytes at relatively lower concentrations than detectors typically used in conjunction with drilling operations. For example, the sensors 200, 600 may be capable of detecting concentrations of analytes in the fluid 201 of less than about 1,000 ppm (parts per million), less than about 500 ppm, less than about 250 ppm, less than about 100 ppm, less than about 20 ppm, or even less than about 5 ppm. Thus, the sensors 200, 600 may enable testing that is not feasible or accurate with conventional sensors.

Additional non limiting example embodiments of the disclosure are described below.

Embodiment 1

A method of detecting an analyte, comprising vaporizing at least a portion of a fluid within a wellbore, passing the vaporized fluid adjacent a chemiresistive sensing element coupled to a drill string within the wellbore, and sensing a resistivity of the chemiresistive sensing element.

Embodiment 2

The method of Embodiment 1, wherein sensing a resistivity of the chemiresistive sensing element comprises measuring at least one of a current passing through the chemiresistive sensing element and a voltage drop across the chemiresistive element.

Embodiment 3

The method of Embodiment 1 or Embodiment 2, wherein vaporizing at least a portion of a fluid within the wellbore comprises vaporizing a gas dissolved in a liquid.

Embodiment 4

The method of any of Embodiments 1 through 3, wherein vaporizing at least a portion of a fluid within the wellbore comprises separating hydrogen sulfide from at least one hydrocarbon.

Embodiment 5

The method of Embodiment 4, wherein separating hydrogen sulfide from at least one hydrocarbon comprises vaporizing the hydrogen sulfide while the at least one hydrocarbon remains in a liquid phase.

Embodiment 6

The method of any of Embodiments 1 through 5, wherein vaporizing at least a portion of a fluid within the wellbore comprises reducing a total pressure acting on the fluid.

Embodiment 7

The method of Embodiment 6, wherein reducing a total pressure on the fluid comprises reducing the total pressure acting on the fluid to an expansion ratio of at least about 60.

Embodiment 8

The method of any of Embodiments 1 through 7, wherein vaporizing at least a portion of a fluid within the wellbore comprises moving a piston to expand a volume in which the fluid is contained.

Embodiment 9

The method of any of Embodiments 1 through 8, wherein vaporizing at least a portion of a fluid within the wellbore comprises passing the fluid through a venturi tube.

Embodiment 10

The method of any of Embodiments 1 through 9, wherein passing the vaporized fluid adjacent a chemiresistive sensing element within a wellbore comprises passing at least one component of the gaseous portion of the fluid through a membrane selective to the transfer of the at least one component of the vaporized fluid.

Embodiment 11

A sensor for detecting an analyte comprising an expansion device for vaporizing a portion of a fluid within a wellbore, a chemiresistive sensing element configured to contact the vaporized fluid within the wellbore and a controller configured to pass a current through the chemiresistive sensing element and calculate a resistance of the chemiresistive sensing element in contact with the gaseous portion of the fluid.

Embodiment 12

The sensor of Embodiment 11, wherein the chemiresistive sensing element comprises a material selected from the group consisting of gold, silver, copper, and alloys and mixtures thereof.

Embodiment 13

The sensor of Embodiment 11, wherein the chemiresistive sensing element comprises a material selected from the group consisting of zinc oxide, tungsten oxides, and mixtures thereof.

Embodiment 14

The sensor of Embodiment 11, wherein the chemiresistive sensing element comprises a material selected from the group consisting of polymers or polymer-matrix composite materials, and mixtures thereof.

Embodiment 15

The sensor of any of Embodiments 11 through 14, wherein the expansion device comprises a piston configured to move to expand a volume in which the fluid is contained.

Embodiment 16

The sensor of any of Embodiments 11 through 15, wherein the expansion device comprises a venturi tube.

Embodiment 17

The sensor of any of Embodiments 11 through 16, further comprising a semipermeable membrane over the chemiresistive sensing element.

Embodiment 18

The sensor of Embodiment 17, wherein the semipermeable membrane is configured to selectively allow transfer of a gaseous species at a higher rate than a liquid species.

Embodiment 19

The sensor of Embodiment 17 or Embodiment 18, wherein the semipermeable membrane is configured to selectively allow transfer of hydrogen sulfide at a higher rate than a hydrocarbon.

Embodiment 20

The sensor of any of Embodiments 11 through 19, further comprising an electrical detector comprising a plurality of electrodes in electrical contact with the chemiresistive sensing element.

Embodiment 21

The sensor of any of Embodiments 11 through 20, further comprising a heater for vaporizing at least a portion of the fluid before contacting the vaporized fluid with the chemiresistive element.

Embodiment 22

The sensor of any of Embodiments 11 through 21, wherein the chemiresistive element is configured to detect an analyte selected from the group consisting of hydrogen sulfide, carbon monoxide, carbon dioxide, and ammonia.

Embodiment 23

The sensor of Embodiment 22, wherein the chemiresistive element is configured to detect hydrogen sulfide having a concentration of less than about 500 ppm.

Embodiment 24

An earth-boring tool comprising a bit body coupled to a drill string and the sensor of any of Embodiments 11 through 23.

Embodiment 25

A method of detecting an analyte, comprising passing a portion of a fluid to a chemiresistive sensing element through a semipermeable membrane, wherein the chemiresistive sensing element is coupled to a drill string within a wellbore, and sensing a resistivity of the chemiresistive sensing element.

Embodiment 26

A sensor for detecting an analyte, comprising a chemiresistive sensing element configured to contact a vapor within a wellbore; a semipermeable membrane covering the chemiresistive sensing element and configured to protect the chemiresistive sensing element from liquids; and a controller configured to pass a current through the chemiresistive sensing element and calculate a resistance of the chemiresistive sensing element in contact with the vapor.

While the present disclosure has been described with respect to certain illustrated embodiments, those of ordinary skill in the art will recognize and appreciate that it is not so limited. Rather, many additions, deletions, and modifications to the illustrated embodiments may be made without departing from the scope of the invention as hereinafter claimed, including legal equivalents thereof. In addition, features from one embodiment may be combined with features of another embodiment while still being encompassed within the scope of the invention. Further, embodiments of the disclosure have utility with different and various drilling tool types and configurations.

What is claimed is:

1. A method of detecting an analyte, comprising:
passing a vapor within a wellbore adjacent a chemiresistive sensing element within the wellbore, the chemiresistive sensing element comprising a wire having a diameter of less than about 1 μm, the chemiresistive sensing element configured such that a resistivity of the chemiresistive sensing element changes in response to a presence of the analyte in the vapor in proximity to the chemiresistive sensing element;
protecting the chemiresistive sensing element from liquids with a semi-permeable membrane covering the chemiresistive sensing element; and
calculating the resistivity of the chemiresistive sensing element in contact with the vapor with a controller located within the chemiresistive sensing element and configured to pass a current through the chemiresistive sensing element.

2. The method of claim 1, wherein calculating the resistivity of the chemiresistive sensing element comprises measuring at least one of the current passing through the chemiresistive sensing element and a voltage drop across the chemiresistive sensing element.

3. The method of claim 1, wherein passing the vapor within a wellbore adjacent a chemiresistive sensing element comprises passing at least a portion of the vapor through a membrane selective to transfer of at least one component of the vapor.

4. The method of claim 1, further comprising forming at least a portion of the vapor within the wellbore by vaporizing a gas dissolved in a liquid.

5. The method of claim 4, wherein forming at least a portion of the vapor within the wellbore comprises moving a piston to expand a volume in which the liquid is contained.

6. The method of claim 4, wherein forming at least a portion of the vapor within the wellbore comprises passing the liquid with the gas dissolved therein through a venturi tube.

7. The method of claim 1, further comprising separating at least one hydrocarbon from the vapor before passing the vapor adjacent the chemiresistive sensing element.

8. The method of claim 7, wherein separating the at least one hydrocarbon from the vapor comprises vaporizing hydrogen sulfide while at least a portion of the at least one hydrocarbon remains in a liquid phase.

9. A sensor for detecting an analyte, comprising:
a chemiresistive sensing element configured to contact a vapor within a wellbore, the chemiresistive sensing element comprising a wire having a diameter of less than about 1 μm, wherein a resistivity of the chemiresistive sensing element changes in response to a presence of the analyte in the vapor in proximity to the chemiresistive sensing element;
a semipermeable membrane covering the chemiresistive sensing element and configured to protect the chemiresistive sensing element from liquids; and
a controller located within the chemiresistive sensing element and configured to pass a current through the chemiresistive sensing element and calculate the resistivity of the chemiresistive sensing element in contact with the vapor.

10. The sensor of claim 9, wherein the chemiresistive sensing element comprises at least one material selected from the group consisting of gold, silver, copper, and alloys and mixtures thereof.

11. The sensor of claim 9, wherein the semipermeable membrane is configured to selectively allow transfer of a gaseous species at a higher rate than a liquid species.

12. The sensor of claim 9, further comprising a heater configured to form at least a portion of the vapor before the vapor contacts the chemiresistive sensing element.

13. The sensor of claim 9, wherein the chemiresistive sensing element is configured to detect hydrogen sulfide having a concentration of less than about 500 ppm.

14. The sensor of claim 9, further comprising an expansion device in fluid communication with the chemiresistive sensing element, the expansion device configured to vaporize a portion of a fluid to form at least a portion of the vapor within a the wellbore before the vapor contacts the chemiresistive sensing element.

15. The sensor of claim 14, wherein the expansion device comprises a piston configured to move to expand a volume in which the fluid is contained.

16. A tool for forming or servicing a wellbore, comprising:
a body; and
a sensor coupled to the body, the sensor comprising:
a chemiresistive sensing element configured to contact a vapor within the wellbore, the chemiresistive sensing element comprising a wire having a diameter of less than about 1 μm, the chemiresistive sensing element configured such that a resistivity of the chemiresistive sensing element changes in response to a presence of an analyte in the vapor in proximity to the chemiresistive sensing element;
a semi-permeable membrane covering the chemiresistive sensing element and configured to protect the chemiresistive sensing element from liquids; and
a controller located within the chemiresistive sensing element and configured to pass a current through the chemiresistive sensing element and calculate the resistivity of the chemiresistive sensing element in contact with the vapor.

17. The tool of claim 16, further comprising an expansion device in fluid communication with the chemiresistive sensing element, the expansion device configured to vaporize a portion of a fluid to form at least a portion of the vapor within the wellbore before the vapor contacts the chemiresistive sensing element.

18. The tool of claim 17, wherein the expansion device is configured to decrease a pressure on the fluid.

19. The tool of claim 16, wherein the chemiresistive sensing element is configured to detect hydrogen sulfide having a concentration of less than about 500 ppm.

* * * * *